United States Patent
Hurd

(10) Patent No.: US 10,918,772 B1
(45) Date of Patent: Feb. 16, 2021

(54) SOLID STATE HEART ASSIST DEVICE

(71) Applicant: Dillon Gene Hurd, Roland, IA (US)

(72) Inventor: Dillon Gene Hurd, Roland, IA (US)

( * ) Notice: Subject to any disclaimer, the term of this patent is extended or adjusted under 35 U.S.C. 154(b) by 66 days.

(21) Appl. No.: 16/139,811

(22) Filed: Sep. 24, 2018

Related U.S. Application Data

(63) Continuation-in-part of application No. 15/458,238, filed on Mar. 14, 2017, now abandoned.

(60) Provisional application No. 62/324,022, filed on Apr. 18, 2016, provisional application No. 62/307,638, filed on Mar. 14, 2016.

(51) Int. Cl.
*A61M 1/12* (2006.01)
*A61M 1/10* (2006.01)

(52) U.S. Cl.
CPC .......... *A61M 1/1055* (2014.02); *A61M 1/122* (2014.02); *A61M 1/127* (2013.01); *A61M 1/1068* (2013.01); *A61M 1/1086* (2013.01)

(58) Field of Classification Search
CPC ................ A61M 1/1086; A61M 1/122; A61M 2205/3306; A61M 2205/3375; A61M 2205/3523; A61M 2205/3606; A61M 2205/50; A61M 2205/502; A61M 2205/52; A61M 2205/8206; A61M 2205/8243; A61M 2230/005; A61M 2230/04; A61M 2230/20; A61M 2230/30; A61M 2230/50; A61M 2230/63; A61M 1/1055; A61M 1/127

See application file for complete search history.

(56) References Cited

U.S. PATENT DOCUMENTS

| | | | |
|---|---|---|---|
| 5,089,017 A | 2/1992 | Young | |
| 5,161,540 A | 11/1992 | Fehling | |
| 5,498,228 A | 3/1996 | Royalty | |
| 6,595,762 B2 | 7/2003 | Khanwilkar et al. | |
| 2005/0075693 A1* | 4/2005 | Toy | A61N 1/37211 607/60 |
| 2008/0045777 A1 | 2/2008 | Jassawalla et al. | |
| 2011/0092761 A1* | 4/2011 | Almog | A61F 2/2481 600/16 |
| 2012/0323318 A1 | 12/2012 | Yusuf et al. | |
| 2016/0325033 A1 | 11/2016 | Cohen et al. | |

FOREIGN PATENT DOCUMENTS

| | | |
|---|---|---|
| DE | 4314269 | 4/1993 |
| GB | 2477276 | 8/2011 |
| TW | 201105312 | 2/2011 |

* cited by examiner

*Primary Examiner* — George Manuel
(74) *Attorney, Agent, or Firm* — David M. Breiner; BrownWinick Law Firm

(57) ABSTRACT

Disclosed is a control system having a processor configured to control a plurality of electromagnets to assist heart contractions and expansions based on input received from an electrocardiogram electrode and blow flow sensors.

13 Claims, 12 Drawing Sheets

SOLID STATE HEART ASSIST DEVICE

PRIORITY STATEMENT

This application is a continuation-in-part application of U.S. patent application Ser. No. 15/458,238 which was filed with the United States Patent and Trademark Office on Mar. 14, 2017 which in turn claims the benefit of U.S. Patent Application No. 62/307,638 which was filed on Mar. 14, 2016 with the United States Patent and Trademark Office and U.S. Patent Application No. 62/324,022 which was filed on Apr. 18, 2016 with the United States Patent and Trademark Office, the entire contents of each of which are herein incorporated by reference.

BACKGROUND

1. Field

Example embodiments relate to an electromagnetic pumping system and control system and more particularly to a pump and control system that moves fluid through cavities and valves using electromagnets controlled by a control processor unit. The pump and control system may be embodied in many useful forms such as, but not limited to, a heart assist device.

2. Description of the Related Art

In the United States alone, more than 735,000 heart attacks occur annually, with 5.7 million adults suffering from heart failure. Every year, $110 billion dollars are spent treating heart attacks, and the total direct medical costs of cardiovascular disease are projected to increase from $396 billion in 2012 to $918 billion in 2030. There is a substantial need for a solution to more effectively treat and resolve the problem, as heart failure remains one of the greatest costs and challenges facing our country's health.

The current, state-of-the-art ventricular assist devices (VADs) are implantable turbine pumping systems that require invasive surgeries and external electrical leads, which are prone to infection. Currently, other companies are attempting to improve these devices by reducing their size. However, there are limitations to this approach. For example, the current pumps are limited by the minimum tube size needed to move 5 L/min of blood at an appropriate pressure. Thrombosis is the most significant problem, and regardless of how small the turbine is, the turbine will still shear blood cells and create an immune response. The issues discussed above are only some of the inherent constraints of the current VADs available.

SUMMARY

The inventor is transforming the traditional thinking regarding VADs to create the next generation of devices, which addresses the problems with current technologies while adding other innovative features. Inventor's novel electromagnetic pumping system (EMPS) addresses the issue of thrombosis through its lack of moving parts, which greatly reduces biocompatibility risks. The EMPS may be composed of small flexible components that may be anchored nondestructively to the heart through a minimally invasive surgical approach.

Example embodiments provide a pump and control system. In one nonlimiting example embodiment, the EMPS and control system is configured as a device to gently handle fluid for use in assisting the natural heart in contraction or to contract an artificial heart. The device may assist a failing heart by using a number of electromagnets (EM) on the surface of the heart which interact with permanent magnets (PM) implanted in the heart. If the heart is too damaged for this, the ventricles of the heart may be replaced with artificial ventricles and the electromagnets and permanent magnets may power the artificial heart in the same way it assists the natural heart.

In example embodiments, a control unit may control the device with little to no input from a user or caregiver through advance adaptive control algorithms and or neural network pattern recognition programs.

In example embodiments, an implanted power storage system may allow for wireless changing for the device by providing a backup that will run the devices when wireless charging is not occurring. This will allow the devices it to be fully implanted reducing risks of infection and physical trauma while increasing patient quality of life.

BRIEF DESCRIPTION OF THE DRAWINGS

Example embodiments are described in detail below with reference to the attached drawing figures, wherein.

DETAILED DESCRIPTION

Figure 1:
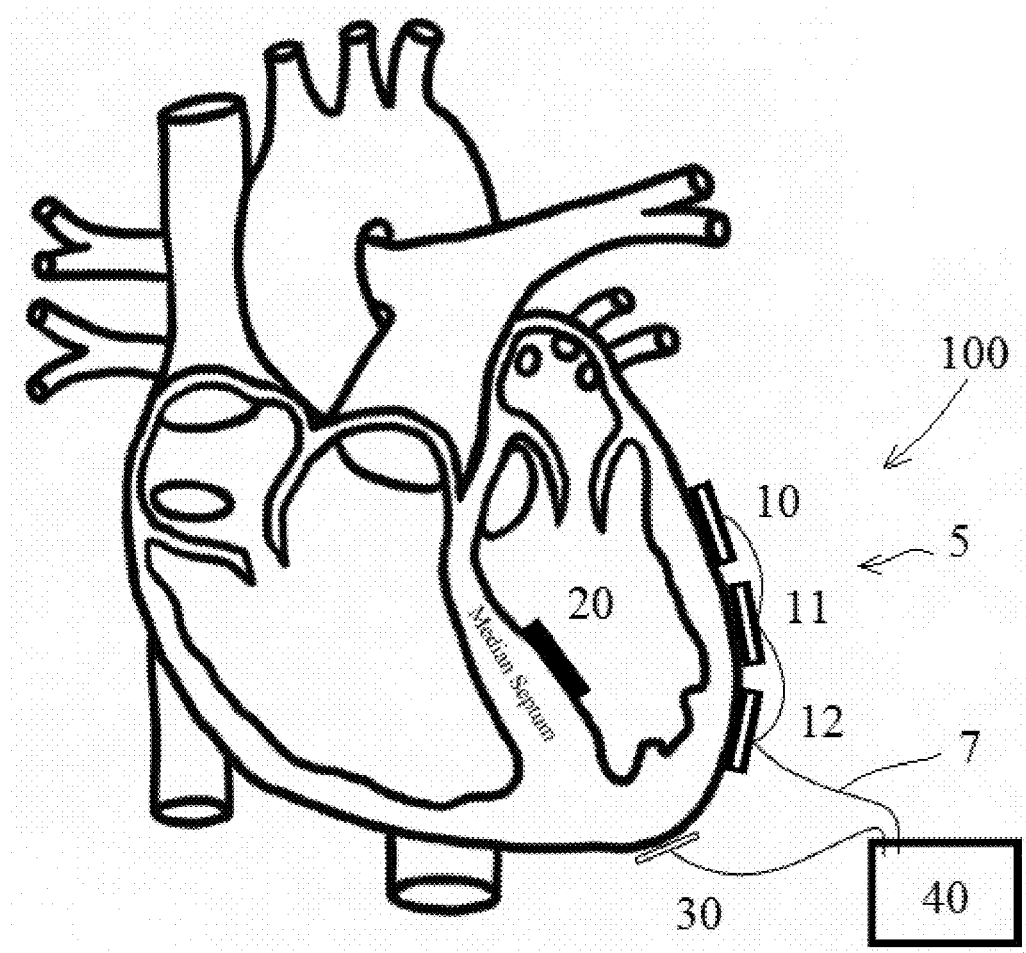
FIG. 1 is a cross section view of a heart with a left ventricular assist device in accordance with example embodiments.

Example embodiments will now be described more fully with reference to the accompanying drawings, in which example embodiments of the invention are shown. The invention may, however, be embodied in different forms and should not be construed as limited to the embodiments set forth herein. Rather, these embodiments are provided so that this disclosure will be thorough and complete, and will fully convey the scope of the invention to those skilled in the art. In the drawings, the sizes of components may be exaggerated for clarity.

It will be understood that when an element or layer is referred to as being "on," "connected to," or "coupled to"

another element or layer, it can be directly on, connected to, or coupled to the other element or layer or intervening elements or layers that may be present. In contrast, when an element is referred to as being "directly on," "directly connected to," or "directly coupled to" another element or layer, there are no intervening elements or layers present. As used herein, the term "and/or" includes any and all combinations of one or more of the associated listed items.

It will be understood that, although the terms first, second, etc. may be used herein to describe various elements, components, regions, layers, and/or sections, these elements, components, regions, layers, and/or sections should not be limited by these terms. These terms are only used to distinguish one element, component, region, layer, and/or section from another elements, component, region, layer, and/or section. Thus, a first element component region, layer or section discussed below could be termed a second element, component, region, layer, or section without departing from the teachings of example embodiments.

Spatially relative terms, such as "beneath," "below," "lower," "above," "upper," and the like, may be used herein for ease of description to describe one element or feature's relationship to another element(s) or feature(s) as illustrated in the figures. It will be understood that the spatially relative terms are intended to encompass different orientations of the structure in use or operation in addition to the orientation depicted in the figures. For example, if the structure in the figures is turned over, elements described as "below" or "beneath" other elements or features would then be oriented "above" the other elements or features. Thus, the exemplary term "below" can encompass both an orientation of above and below. The structure may be otherwise oriented (rotated 90 degrees or at other orientations) and the spatially relative descriptors used herein interpreted accordingly.

Embodiments described herein will refer to plan views and/or cross-sectional views by way of ideal schematic views. Accordingly, the views may be modified depending on manufacturing technologies and/or tolerances. Therefore, example embodiments are not limited to those shown in the views, but include modifications in configurations formed on the basis of manufacturing process. Therefore, regions exemplified in the figures have schematic properties and shapes of regions shown in the figures exemplify specific shapes or regions of elements, and do not limit example embodiments.

The subject matter of example embodiments, as disclosed herein, is described with specificity to meet statutory requirements. However, the description itself is not intended to limit the scope of this patent. Rather, the inventors have contemplated that the claimed subject matter might also be embodied in other ways, to include different features or combinations of features similar to the ones described in this document, in conjunction with other technologies. Generally, example embodiments relate to a pump and control system and more particularly to a pump and control system that moves fluid through cavities and valves using electromagnets controlled by a control processor unit. The pump and control system may be embodied in many useful forms such as, but not limited to, a heart assist device.

Figure 2:
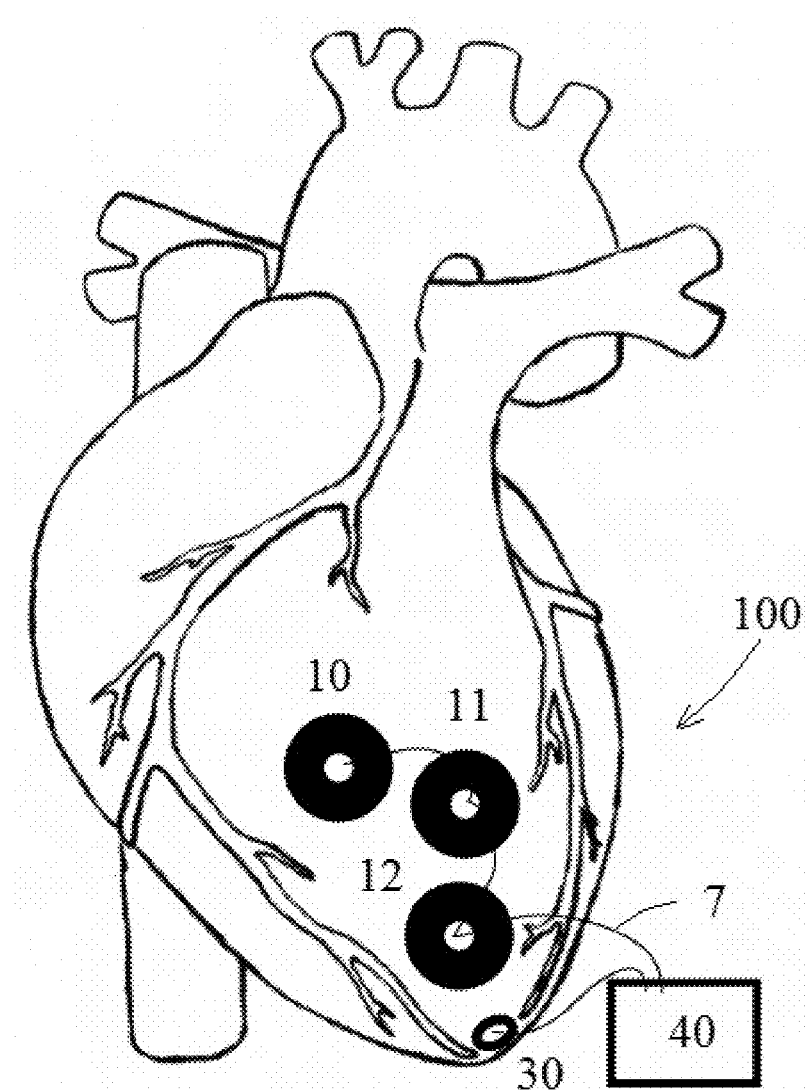
FIG. 2 is an external view of the heart with the left ventricular assist device in accordance with example embodiments.

FIGS. 1 and 2 illustrate an example of a device 100 configured to operate as a left ventricular assist device. As shown in FIGS. 1 and 2, the device 100 may include a first plurality of electromagnets 5 which may be placed on an exterior surface of a left ventricle. The first plurality of electromagnets 5 may include a first electromagnet 10, a second electromagnet 11, and a third electromagnet 12, however, the first plurality of electromagnets 5 may include more than three electromagnets or less than three electromagnets. In other words, the number of electromagnets is not critical.

In example embodiments, the first plurality of electromagnets 5 may be flexible and may bend and move with the natural motion of the heart beating. The first plurality of electromagnets 5 may be housed in a flexible material with cavities and valves that will allow for the movement of a cooling fluid through the housing to discharge heat generated be the electromagnets 5. The first plurality of electromagnets 5 may be connected by a lead 7 to a control system 40. A first permanent magnet 20, may be on the interior of the left ventricle and may be anchored to the median septum of the natural heart or implanted within the median septum of the natural heart. The permanent magnet 20 (and the permanent magnets 22-23, to be explained shortly) may be made from rare earth metals such as neodymium or from other highly magnet materials which may be in the form of powder or small pieces to allow them to be flexible. That is, permanent magnet 20 may be comprised of smaller magnets. Other materials that could be used are super magnetic nanoparticles, alloyed metals that may increase magnetic properties. Magnetic liquids may also be used to make the permanent magnet 20 (and the permanent magnets 21-23) very flexible and to allow it to be easily implanted endoscopically. The permanent magnet 20 may be coated in a soft flexible material like silicon which may be infused with chemicals to encourage cells to grow over the material to help the permanent magnet 20 anchor to the heart wall. The permanent magnet may also be anchored with stitches and or barred anchors to reduce the risk of detachment. The risk of detachment may be addressed by implanting the permanent magnet 20 inside the median septum of the natural heart. When the permanent magnet 20 is implanted in the median septum of the natural heart it may be done through a catheter that will insert a balloon which will the be filled with magnet materials suspended in a binder. After the catheter has implanted the balloon filled magnet materials suspended in a binder the electromagnets 5 can be energized to align the magnet materials polarity to be opposite that if the electromagnets 5. This alignment process can be used to customize the permanent magnet 20 to match up with the electromagnets 5 for and given heart ventricle both artificial or natural. The permanent magnets in the total assist model 200 (to be explained later) may be on opposite side of the median septum and may be aligned so they pull towards one another to help them stay anchored. As one skilled in the art will readily recognize, more than one permanent magnet may be used on each chamber of the heart if needed. The device 100 may further include an electrocardiogram electrode 30, placed on the exterior of the heart and connected to the control system 40. The electrocardiogram (ECG) electrode 30 may provide input about the state of the heart such as, but not limited to, the heart rate. The ECG electrode may feed the control system 40 with a relatively full picture of the heart as it is beating, however, in some embodiments, more than one ECG electrode may be used depending on the model and need based on the patient. The data from the ECG electrodes may be used with a neural network type program in the control system 40 to allow for the control system 40 to recognize patterns in the heart and make the changes. The ECG may help the control system 40 determine the timing that is needed when assisting the heart.

Figure 3:
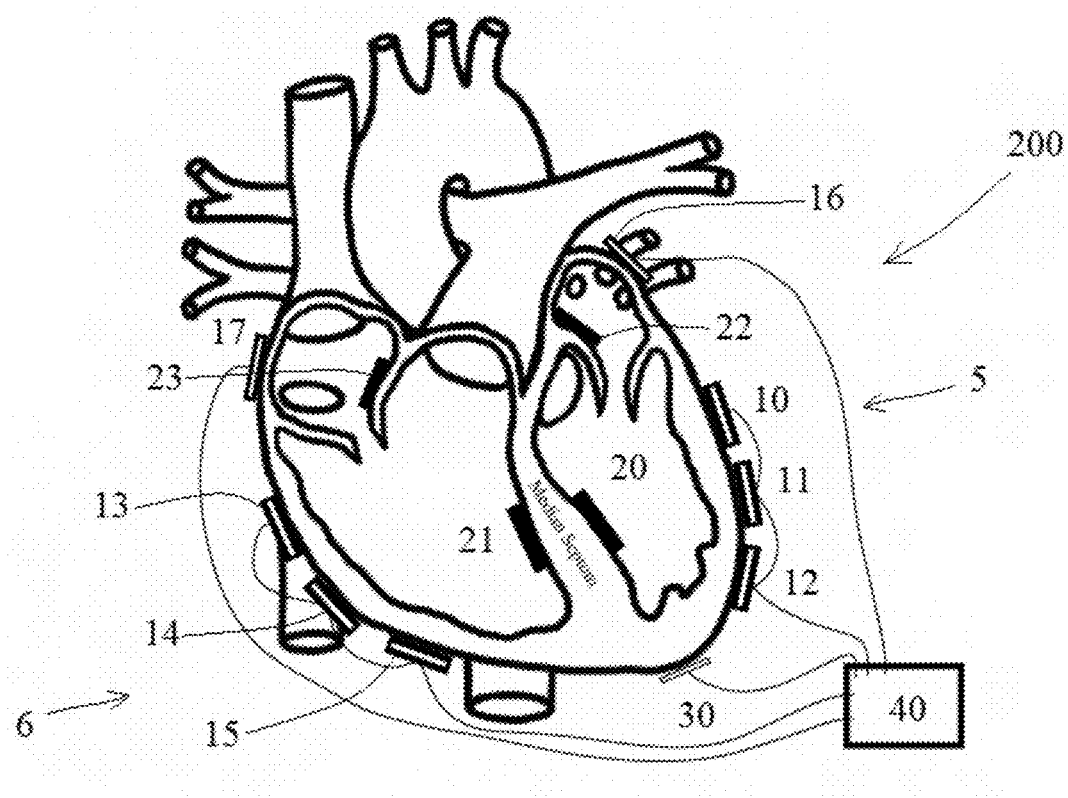
FIG. 3 is a cross section view of a heart with a total heart assist device in accordance with example embodiments.
Figure 4:
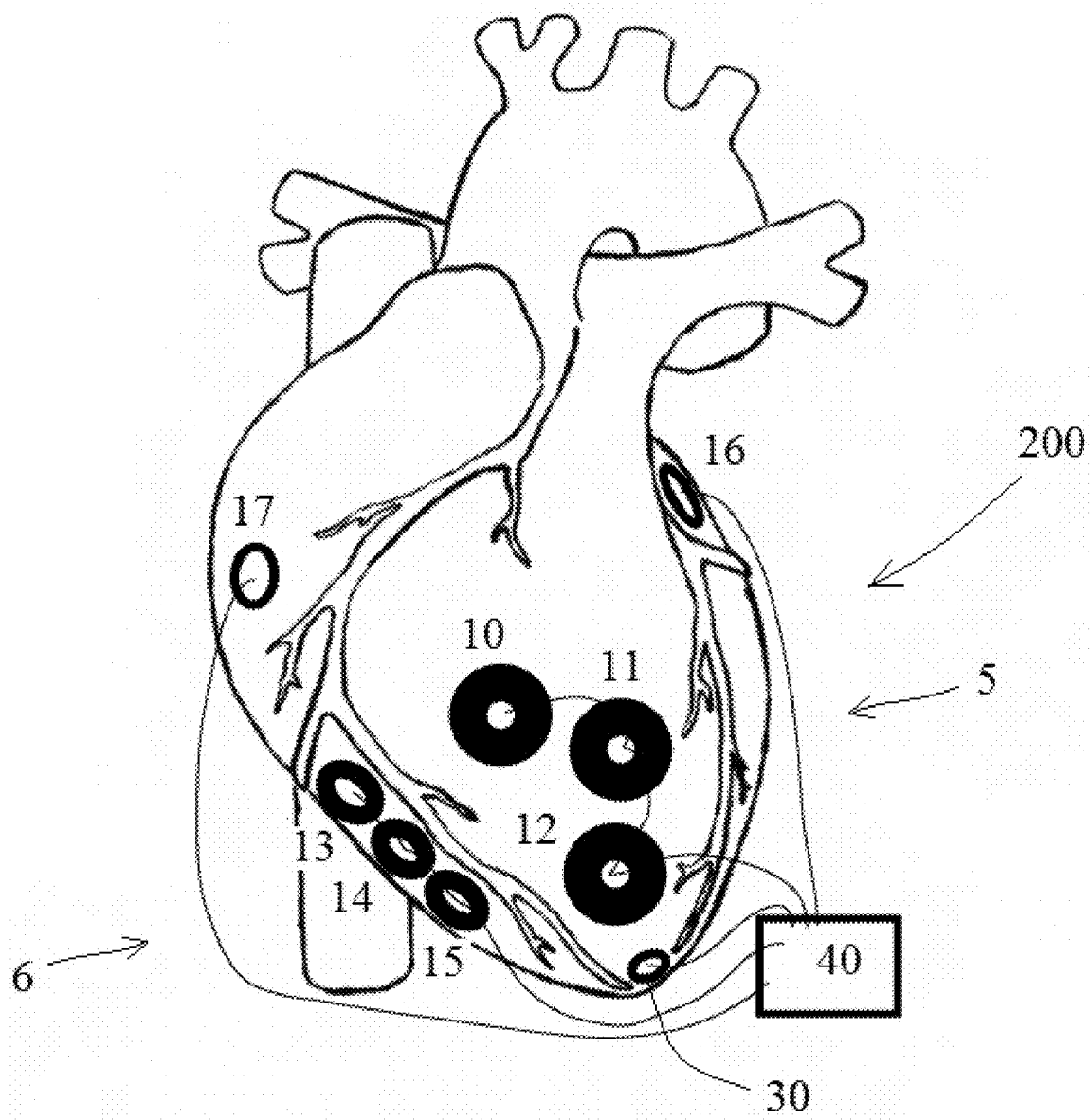
FIG. 4 is an external view of the heart with the total heart assist device in accordance with example embodiments.

FIGS. 3 and 4 illustrate an example of a device 200 configured to operate as a total heart assist device. In FIGS. 3 and 4 a first plurality of electromagnets 5 is placed on the exterior surface of the left ventricle and a second plurality of electromagnets 6 is placed on the exterior surface of the right ventricle. In FIGS. 3 and 4 the first plurality of electromagnets 5 includes a first electromagnet 10, a second electromagnet 11, and a third electromagnet 12 and the second plurality of electromagnets 6 includes a fourth electromagnet 13, a fifth electromagnet 14, and a sixth electromagnet 15. Though FIGS. 3 and 4 illustrate the first and second pluralities of electromagnets 5 and 6 as comprising three electromagnets the number is relatively unimportant. For example, each of the first and second pluralities of electromagnets 5 and 6 may include more than three or less than three electromagnets.

In the nonlimiting example embodiment of FIGS. 3 and 4, the device 200 may include one or more electromagnets 17 on the exterior surface of the right atrium, and one or more electromagnets 16 on the exterior surface of the left atrium. These electromagnets 16 and 17 may be flexible and may bend and move with the natural motion of the heart beating. The electromagnets 16 and 17 may be connected by a lead to the control system 40.

In the nonlimiting example of FIGS. 3 and 4, the device 200 may further include a first permanent magnet 20 that may be attached on the interior of the left ventricle. In this nonlimiting example embodiment the first permanent magnet 20 may be anchored to the median septum of the natural heart. The device 200 may also include second permanent magnet 21 arranged on the interior of the right ventricle and attached to an opposing side of the median septum. The device 200 may also include a third permanent magnet 23 on the interior of the left atrium and a fourth permanent magnet 22 that may be on the interior of the right atrium. These permanent magnets 20, 21, 22, and 23 may be flexible and may be endoscopy implanted. In this nonlimiting example embodiment, the device 200 may further include an electrocardiogram electrode 30, placed on the exterior of the heart and connected to the control system 40, to provide input about the state of the heart.

Figure 5:
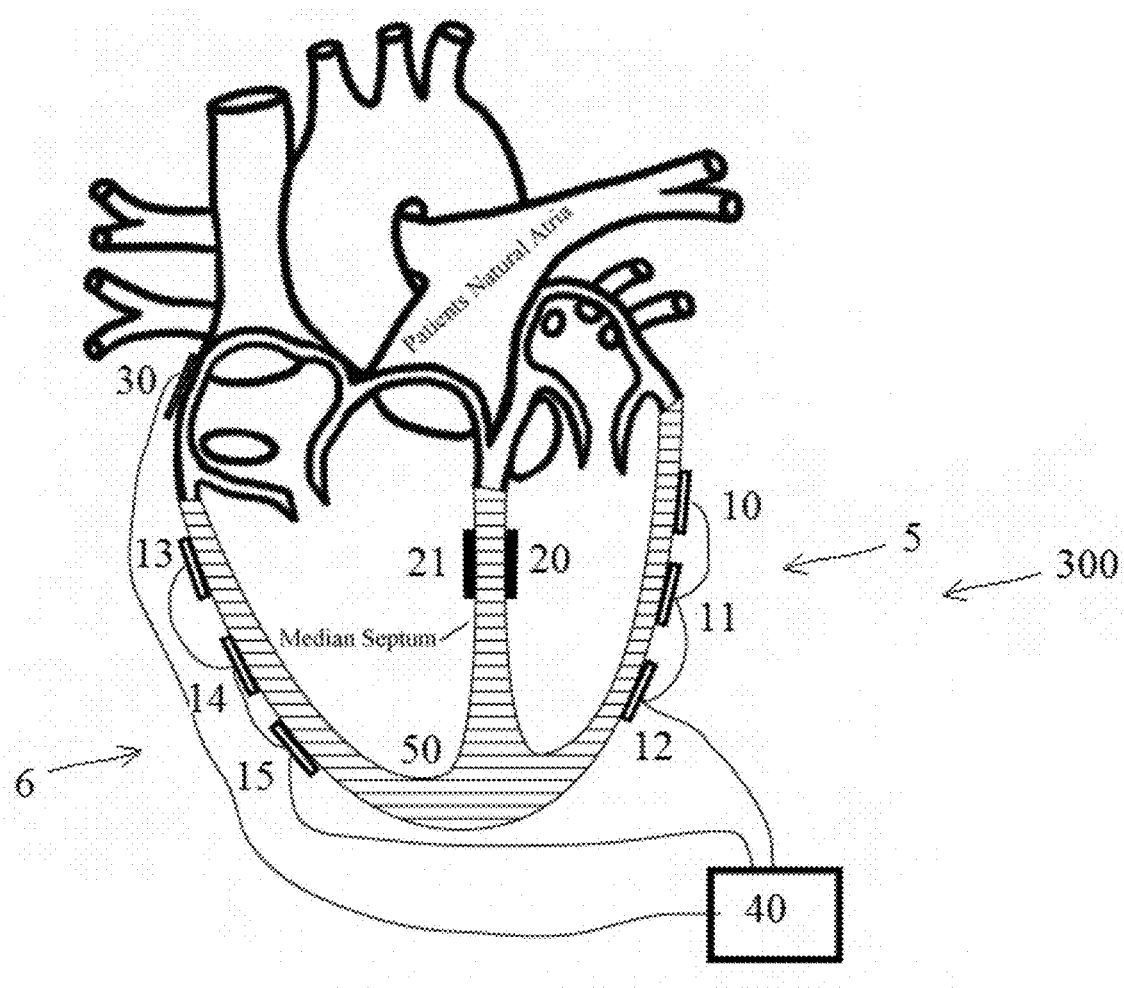
FIG. 5 is a cross section view of an artificial hybrid heart with an assist device in accordance with example embodiments.

FIG. 5 illustrates an example of an artificial heart hybrid with an assist device 300 incorporated therein. The ventricles of this artificial hybrid heart may be artificial 50, but may also have properties that mimic the natural ventricles. The artificial ventricles may be attached to the patient's natural atria and may use the patient's natural valves when possible. The artificial ventricles may be made of a soft bio-compatible material like silicon, or some other polymer or potentially a combination of materials. The artificial ventricle may also be made from synthetic and biological material. This may be done using some tissue from the patient and then reinforcing it with synthetic material. When synthetic and biological materials are used, the synthetic materials may bio-degrade and leave behind a purely biological ventricle. The use of a bio-degradable synthetic ventricle could allow for the regrowth of a biological ventricle from the patient's tissues. This may also come in the form of a extracellular matrix that has been seeded with stem cells. The pumping system would act as a prosthesis as the cells grow and mature. The end result could be the removal of the pumping system and or it could be shut down to be used in future if need be. The artificial ventricles may be powered be the same electromagnetic drive system that is used in devices 100 and 200. For example, a first plurality of electromagnets 5 may be placed on an exterior surface of the artificial left ventricle and a second plurality of electromagnets 6 may be placed on a surface of the artificial right ventricle. The first and second pluralities of electromagnets 5 and 6 may be flexible and may bend and move the artificial ventricles in the natural motion of a heart beating. The pluralities of electromagnets 5 and 6 may be connected by a lead to a control system 40. The device 300 may further include a first permanent magnet 20 on the interior of the left ventricle and may be anchored to the median septum of the artificial ventricles and a second permanent magnet 21 anchored in on the interior of the right ventricle. These permanent magnets 20 and 21 may be flexible to allow for the artificial ventricles to move like that of a natural heart. There may be an electrocardiogram electrode 30, placed on the exterior of the natural part of heart and connected to the control system 40, to provide input about the state of the heart.

In example embodiments, the leads that connect the first and second pluralities of magnets electromagnets 5 and 6 and/or the electromagnets 16 and 17 as well as the leads that connect and the ECG electrode 30 to the control system 40, may be removable to allow for easy replacement in the case of component failure.

Figure 6:
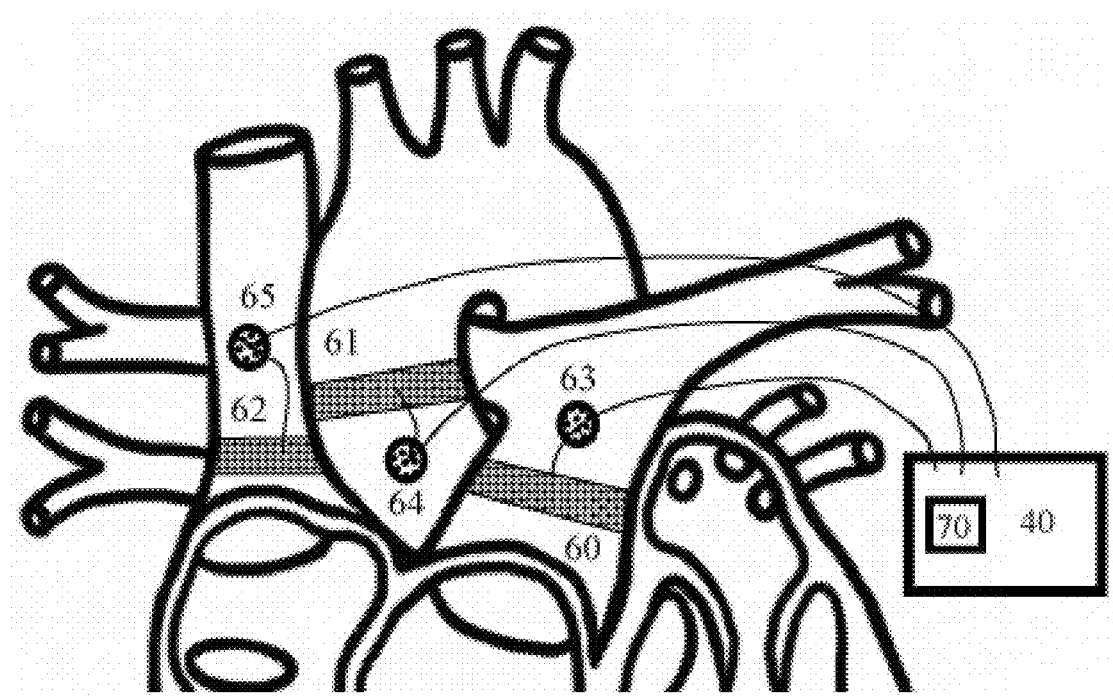
FIG. 6 is a partial view of a heart having various sensors mounted thereon in accordance with example embodiments.

In example embodiments, the heart assist devices 100, 200, and 300 may include a plurality of sensors as shown in FIG. 6. As one example, strain gauges 60, 61, 62 may be placed either within or on the natural veins and arteries of the heart. These strain gauges 60, 61, 62 may be used to determine the blood pressure at the inlets and outlets. As another example, optic/sonic sensor 63, 64, 65 may be a optical, sonic hybrid sensor or just an optical and/or sonic sensor and may be incorporated into the device to detect oxygen within the blood and other biometrics such as velocity of the blood. The strain gauges 60, 61, 62 in combination with the optic/sonic sensor 63, 64 create a unique sensor which allows for real and continuous blood pressure and flow sensing. This is a very advantageous capability to have for controlling heart assist devices and helps to makes these devices safer and more reliable. This sensor configuration could also be very useful in monitoring the patient prior to implantation of a heart assist devices or heart transplant. This means that a sensor array made up of strain gauges and optic/sonic sensors could be implanted independent of the heart assist device to monitor a patient who is at high risk of heart failure. The same power system 110 and control system 80 that will run the heart assist could be used to run the sensor array allowing for rapid installation of the heart assist components when the need arises. The electromagnet driver 90 and back up battery 100 could then be implanted with the heart assist components and control system would then be wirelessly updated to run the electromagnets. This modular approach may allow for the heart assist device to change with the needs of the patient. For example, allowing the patient to go from the left assist version to the full assist version may be accomplished by simply implanting more electromagnets and permanent magnets, connecting them to the driver 90, and updating the control system 40. By the same token if the patient's condition worsens and they start to require more power an additional power system 110 can be implanted to provide this. Because of this all the electrical components may be designed to handle at least twice the load required. Other sensors 70 may be placed within the control system enclosure 40 to detect operational parameters including, but not limited to temperature, movement, and altitude to sense the environment within the body and activity levels.

Figure 7:
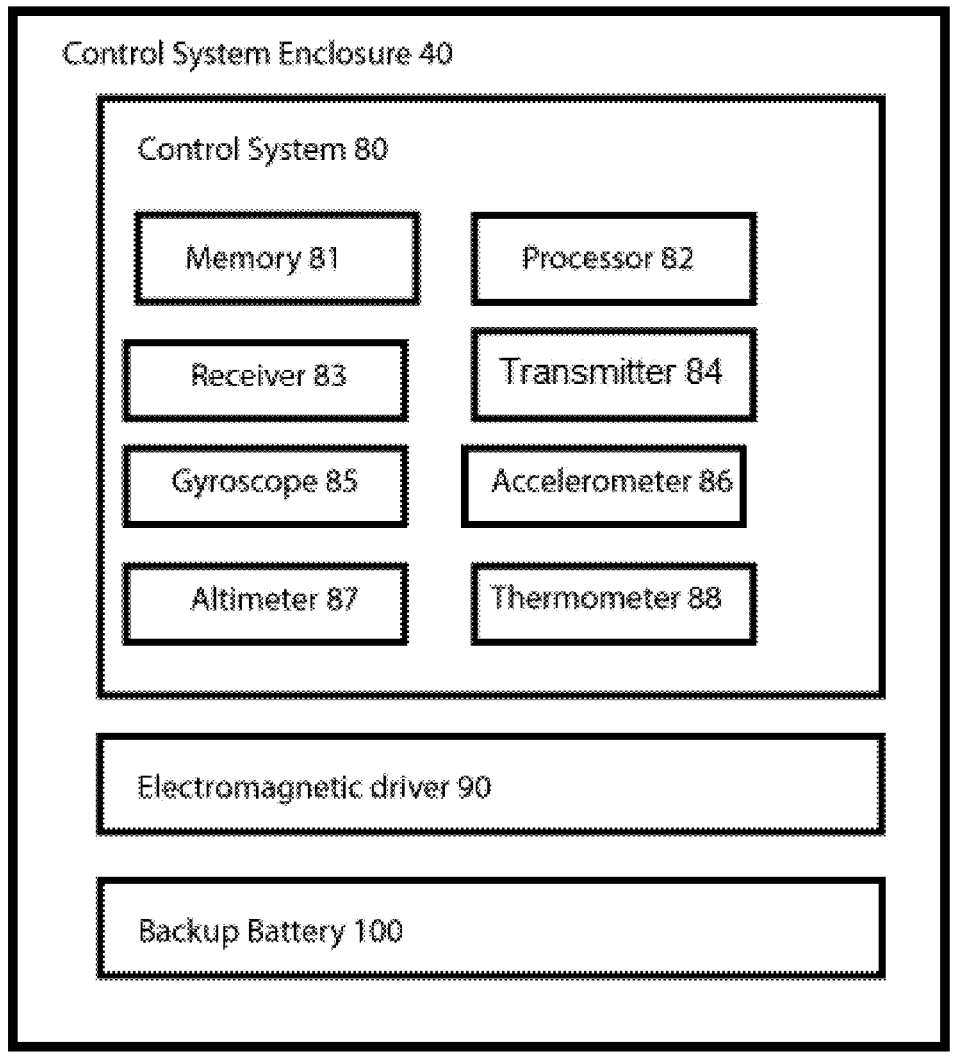
FIG. 7 is a view of control system enclosure with a control system in accordance with example embodiments.

In example embodiments, an advanced control system 80 may be located in a control system enclosure 40 (see FIG. 7). The advanced control system 80 may be connected to the sensors 60-65 and the electromagnets (for example, any one of, or all of, the first and second pluralities of electromagnets 5 and 6 and/or the electromagnets 16 and 17). The control system 80 may have a processor 82 with memory 81, a receiver 83, a transmitter 84, a gyroscope 85 to detect a patient's physical state (i.e., lying down, standing), an accelerometer 86, an altimeter 87 and a thermometer 88. Also, driver 90 for the electromagnets may be in the control system enclosure 40. There may also be a backup battery 100 in the enclosure 40 that may be charged from a primary battery pack 111.

Figure 8:
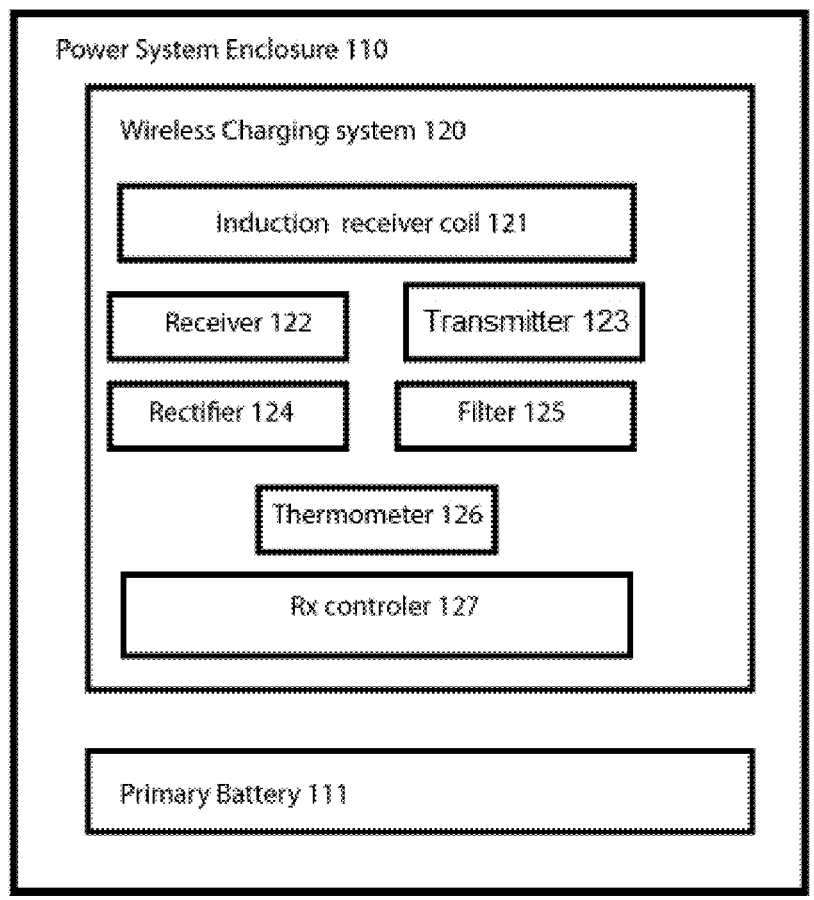
FIG. 8 is a view of a power system enclosure with a wireless charging system in accordance with example embodiments.
Figure 9:
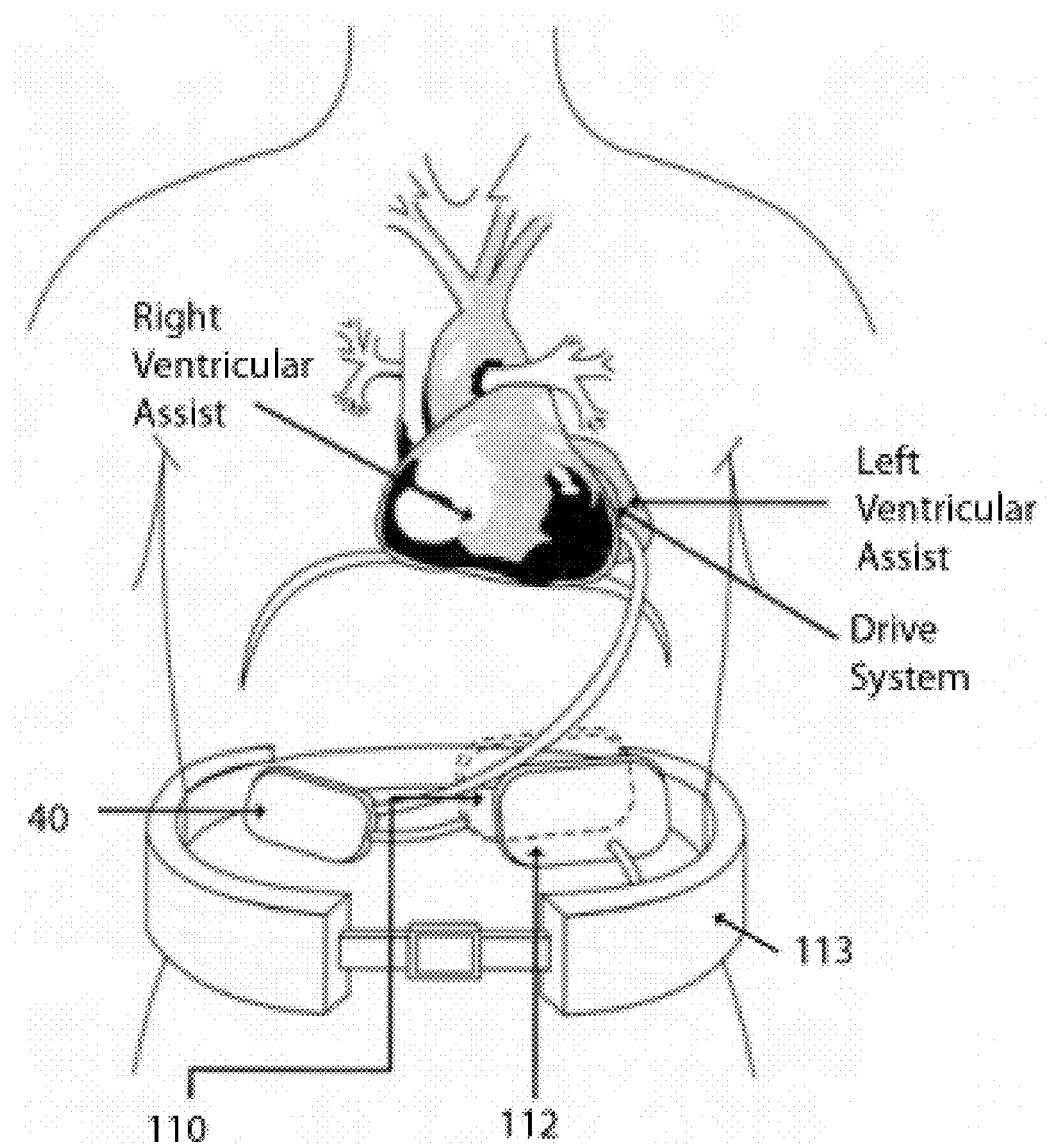
FIG. 9 is a view of an external battery pack in accordance with example embodiments.
Figure 10:
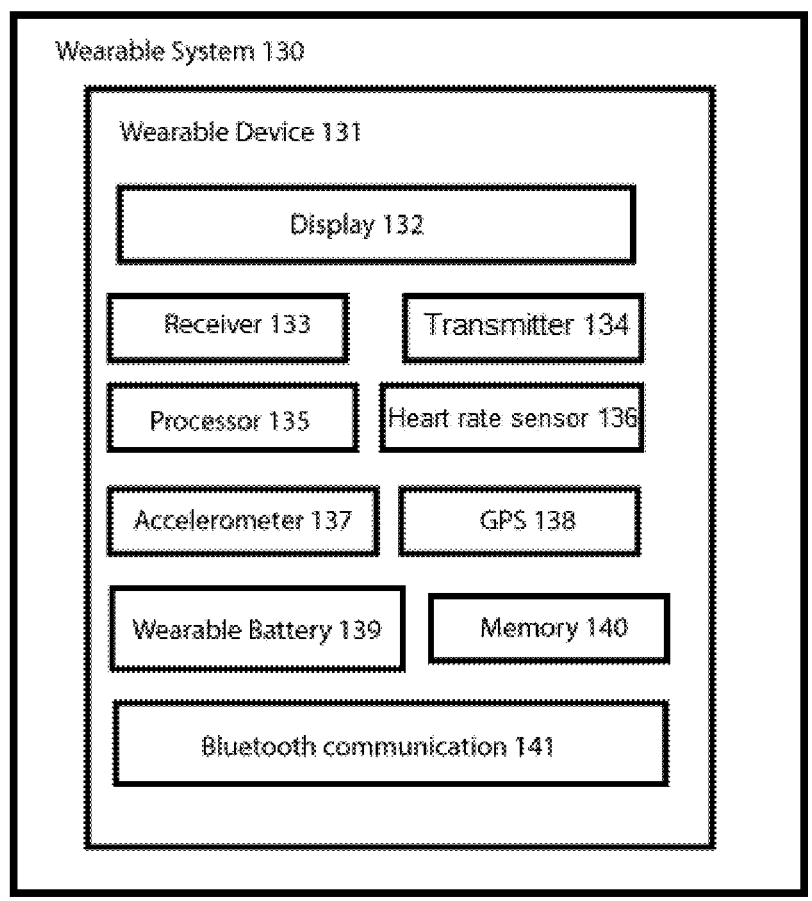
FIG. 10 is a view of wearable system and a wearable device in accordance with example embodiments.
Figure 11:
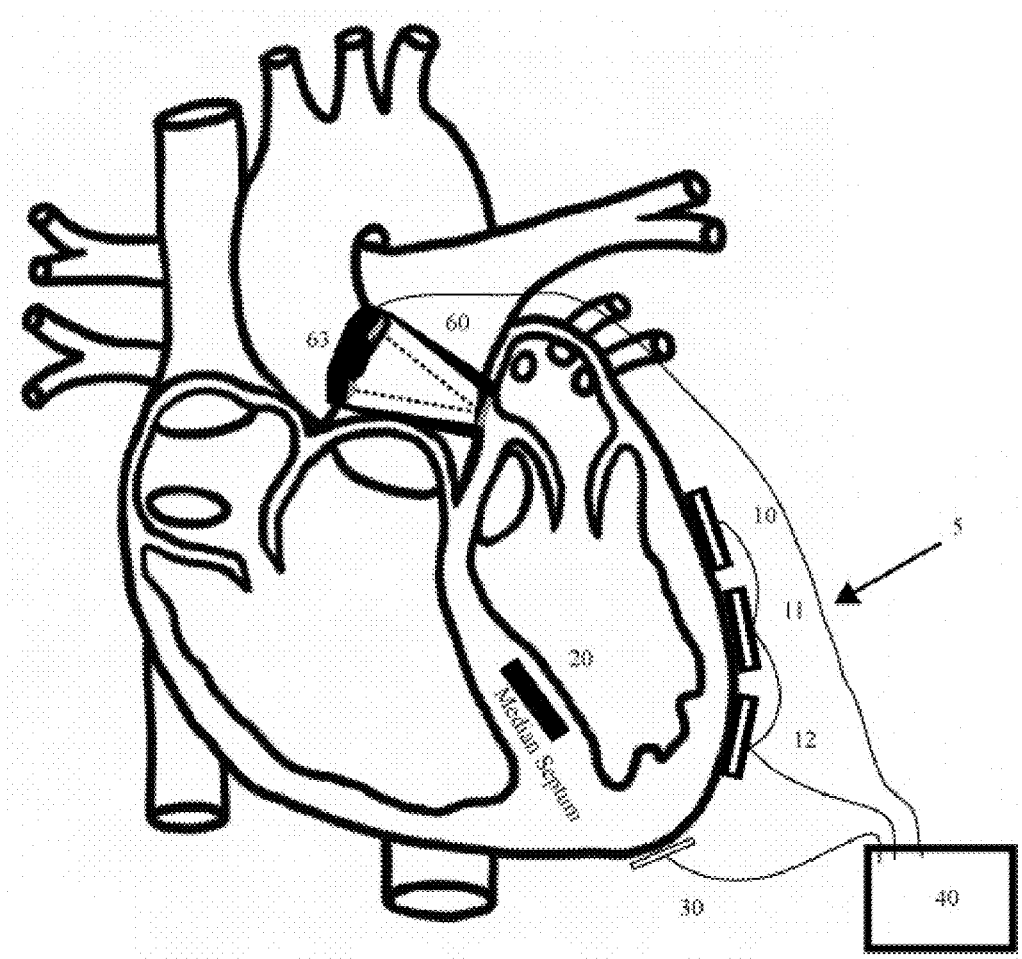
FIG. 11 is a view of a method in accordance with example embodiments.

FIG. 8 illustrates an example of a power system enclosure 110 that will house various power elements. For example, the power system enclosure 110 may house the primary battery 111 and the components of the wireless charging system these components may be built in a way that makes them flexible which would allow for the power system enclosure 110 to also be flexible allowing for less damaging implantation surgery options and made from some flexible bio-compatible material such as silicon. The power system enclosure 110 may be filled will a non-conductive fluid and may be run through a heat exchanger of some sort to help prevent the receiver coil 121 and primary battery 111 from heating up to a point that they may damage the surrounding tissue. This fluid may also be circulated through the flexible housing around the electromagnets 5 to prevent them from overheating and damaging the heart tissue. The wireless charging system 120, for example, may be made up of a receiver coil 121, a receiver 122 that can be used to alert the RX controller 127 that a transmission coil 112 is in place and to start the charging, a transmitter 123 to allow the RX controller 127 to communicate with the external battery pack 113 which can be used to alert the external battery pack 113 that the primary battery is fully charged, to prevent over charging, or the receiving coil 121 or primary battery 111 has reached a dangerous temperature. Also, the wireless charging system 120 may include a rectifier 124 which may convert the current if needed, a signal filter 125 to clean the current when is it received, thermometer 126 to ensure the coil 121 and the RX controller 127 does not get too hot. The RX controller 127 will control the charging process to ensure effectiveness and safety. This wireless charging circuit may be like those used in charging mobile phones and other small electronics. The induction receiver coil 121 may be charged by induction transmission coil 112 which may be powered by the external battery pack 113. The external battery pack 113 may be something that is like a belt of can hang on the waistline of the patient or over their shoulders. This power system 110 may be designed to allow for another power system to be connected in parallel with it in the case more power is needed. It may also be designed in a way to power more than just the heart assist, for example, it could be designed to power other artificial organs or organ support devices. For example, a fully implanted insulin pump could use the same power system 110 as the heart assist reducing the need for an additional surgery. The power system 110 may also be used to power implantable sensors. For example, neural sensors placed on or near the spinal cord to provide neural impulse signals to a prosthetic may be powered be the same power system 110. These examples are meant to show that the power and control system may be designed to allow for other devices to be integrated into them to reduce the surgeries needed.

In example embodiments, a wearable system 130 may be wirelessly connected to the control system 40 using near field communication technology. The wearable system 130 may include a wearable device 131, such as a necklace, wrist band, or the like that has a housing and a fastening member. The wearable device 131 may have a display 132 which may be touch screen to allow for easy user interaction connected to a processor 135 which may allow the wearable to decrypt and analyze the data sent from the control system 80. The wearable system 130 may further include a memory 140 which may allow the wearable system 130 to store data sent from the control system 80, a receiver 133 to allow the wearable system 130 to receive data from the control system's transmitter 84, and a transmitter 134 that may allow the wearable device 131 to communicate with the control system 80 and send data from the sensors on the wearable device 131, such as the accelerometer 137 or the GPS 138. Each of the above elements may be powered by a wearable battery 139 which may be interchangeable to prevent the user from having to remove the wearable device 131 for long periods with charging. Also, the wearable system 130 may further include sensors such as, but not limited to, a heart rate sensor 136, accelerometer 137, GPS 138 and altimeter 139 which may use a substantial amount of power making it better to have outside the body. These sensors may aid in providing data to the processor 82 in the control system 80.

The wearable device 131 may be synched to a mobile phone for storage and transmission of information using Bluetooth 141. This data can be used by a doctor or caregiver to monitor the patient. In the event the patient has complications, the doctors can see the condition of the patient and the device remotely. If the patient is not feeling well they can call the doctor and the doctor can see their condition through the connection of the phone to the wearable system 130. If the patient is in danger the caregiver can call emergency services to the location given by the GPS on the wearable system 130. The wearable device 131 may also be synched to a patient monitor system at a health care facility or through other secure internet connected devices depending on the patient's location and needs.

In operation, once the drive system made up of electromagnets (for example, the pluralities of magnets 5 and 6 and the electromagnets 16-17) and permanent magnets 20-23, the control system enclosure 40 and the power system enclosure 120 are implanted, blood may be pumped through the atria and the ventricles of a natural and/or artificial hearts. The sensors 60-65 may monitor operational parameters preferably every half second or more often. Based on operational parameters detected and transmitted from the sensors 60-65 and the ECG electrode 30, the processor 82 of the control system 80 calculates a timing and force which the electromagnetic driver 90 will translate into power to be sent to the electromagnets 10-17 in the appropriate order. For example, in one embodiment, the optic/sonic sensors 60, 61, 62 detect and transmit information to processor 82 about the blood oxygen level and the stain gauges 63, 64, 65 sense a change in blood pressure. When the blood oxygen level or pressure is high as compared to the normal blood oxygen level or blood pressure that has been set and or determined by the neural network program and or predictive control loops, and or feedback control loops or some combination of control loops algorithms, programs and models, as health operation limits for the patient, the power to the electromagnets 10-17 is decreased. When the blood oxygen level, flow and/or pressure is low, as compared to the preset blood oxygen level or blood pressure, the power is increased. In essence, the power sent to the electromagnets determines how much assistance is given or how hard the ventricles and/or atria contract. The force required to assist the heart depends primarily on the patient and their condition. The force needed can also change if the patient's condition worsens or gets better, which is why a control system that can adapt to the patient in real time is essential. The timing is determined from data collected from the ECG electrode and other sensors which senses when the heart beats and transmits to the processor 82 which then activates the electromagnetic drive 90 at the appropriate time.

Once the timing and needed force is calculated by the processor 82, the processor 82 sends a signal to the electromagnetic driver 90 to activate the electromagnets in the contraction order which depends on the version of the device. For example, the electromagnetic driver 90 may fire the electromagnets 10-17 of the second or third device 200 and 300 by switching polarity to first attract permanent magnets 20-23 and reversing polarity to push the permanent magnets 20-23 away. The electromagnet firing order will depend on the version of device. The left assist device 100, for example, may start by activating electromagnet 12 and then activating to electromagnet 11 and then activating electromagnet 10 and the total heart assist device 200 may start by activating electromagnet 17 and then activating electromagnet 15 and then activating electromagnet 14 and then activating electromagnet 13.

The electromagnet firing order will depend on the version of device, the left assist device may start with electromagnet 12 and the full assist device may start with 17. Based on a predetermined or preset delay, the electromagnetic driver 90 activates the next electromagnet in the array in the same manner as previously described to complete a pump cycle. The processor 80, using the sensor inputs from any one of, or all of, the sensors 60-65, may then calculate the force and timing before repeating the process for the next pump cycle. The processor 80 will do this by using control algorithms that will be stored in the memory 81. The processor 80 could also use a neural network program and the data log on the of previous control loops to recognize patterns and make predictions and changes to the control parameters as need be.

If the transmitted blood oxygen level and blood flow and/or blood pressure falls outside of the safe or healthy preset or predetermined range, then the processor 80 defaults to a safe baseline default timing and force. Also, when a disturbance is detected, such as detecting with the accelerometer 86 that an individual has started to run, the processor 80 may calculate the timing and force based on predetermined and/or preset parameters and from the history of the last time such a disturbance occurred.

The processor 80 may also transmit information to the wearable device 131. In one example, the processor 80 transmits information about heart rate, blood oxygen level, and battery level that is received by the wearable device 131 and shown on display 132. The wearable device 131 may also be synched with the mobile phone and/or a patient monitor where information may be transmitted and stored. The receiver 83 in the control system 80 may be used to update the control system 80 wirelessly allowing doctors and care givers to make changes to the system's parameters and download the memory log, when the appropriate access codes are presented. This will also allow the engineers to update the control system programs and algorithms without removing the device from the patient using the same transmitter 84 and receiver 84 the wearable uses to communicate with the control system. The control system 80 may be made on a platform that allows the whole circuit to be flexible. The flexible circuit design for the control system may or may not have solid components like memory that will be connected to a flexible chip which will allow the circuit to bend, this would allow the control system enclosure 40 to also be flexible allowing for less damaging implantation surgery options. The control system enclosure could be a silicon pouch or some other flexible bio-compatible material in which the flexible control system circuit could be, entrapped in the silicon or suspended in a non-conduction fluid. This non-conductive fluid in the control system enclosure could also be used to assist in cooling the processor by moving the fluid though a heat exchanger to disperse heat to the surrounding body.

Example embodiments of the invention have been described in an illustrative manner. It is to be understood that the terminology that has been used is intended to be in the nature of words of description rather than of limitation. Many modifications and variations of example embodiments are possible in light of the above teachings. Therefore, within the scope of the appended claims, the present invention may be practiced otherwise than as specifically described.

Figure 12:
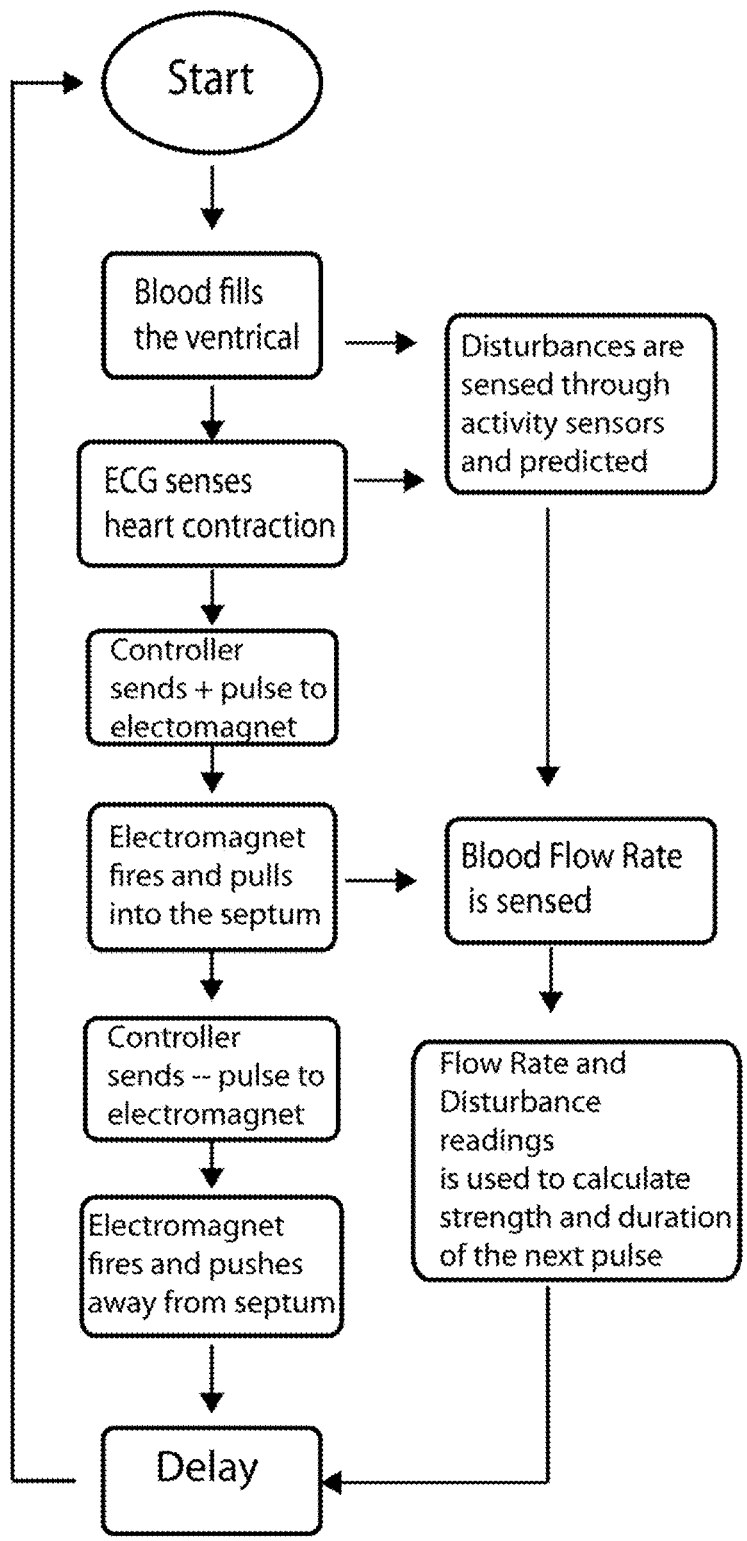
FIG. 12 is a logic flow chart in accordance with example embodiments.

In example embodiments the control system 40 may use data for the ECG 30 but this may not be the primary control variable. The ECG 30 may only be controlling the timing of the energization or contraction of the electromagnets 5. The primary input that the control system 40 *m* use to determine the intensity and duration of the contractions may be based on the output flow from the heart. A normal health human heart outputs between 5-10 L/min. The heart output may be the primary input that the control system 40 may use to control the electromagnets 5. For example, in one embodiment, the optic/sonic sensors 60, 61, 62 detect and transmit information to processor 82 about the blood flow rate out of the heart and the stain gauges 63, 64, 65 sense a change in blood pressure and other activity related feedback. The blood flow rate and disturbances in the form of activity changes will be used to calculate the intensity and duration of the next pulse send to the electromagnets 5 during the next contraction of the heart. A flow chart of what this logic may look like is seen in FIG. 12. From the flow chart FIG. 12 the control system 40 will not need to know when the ventricle is full because the timing of the pulse to the electromagnets 5 is determined by the heart natural contraction timing which is sensed by the ECG 30. The delay between the a+ pulse and the a− pulse may be determined by the flow rate out of the heart. Meaning as the flow rate out stops this indicates the hearts natural contraction is complete and the ventricle is preparing to refill.

Using the data for the optic/sonic sensors 60, 61, 62 and the stain gauges 63, 64, 65 the processor 82 may provide the current state of the heart to the control system 40. The control system 40 may then calculate how much assistance the heart will need from the electromagnets 5 to bring the heart output back a set point. The set point that the control system 40 may be controlling to, may be determined by historical sensor data on the patient and other changes in the condition of the patient. An example of a change in the condition of the patient would be moving from a sitting to a standing position. In this example the control system 40 may receive a signal from the gyroscope 85 and accelerometer 86 that the patient's position has changed, and the control system may increase the set point for heart output to a higher level to prevent the patient from getting light headed after standing quickly. Predictive controls have never been used to control a heart assist device of any kind.

The electromagnets 5 may assist in contraction of the natural or artificial heart by applying force to the outside wall of the ventricle. This force may be created by the magnetic field interactions that pull magnetized components of opposite polarity towards one another. When the electromagnets 5 are energized they may create a magnetic field with the opposite polarity of the permanent magnet 20 and they may be pulled towards one another. The electromagnets 5 may be anchored on the outside of the ventricle and may therefore apply force to the ventricle wall and assist the heart in forcing the blood out of the ventricle, thereby increasing the heart's output. The polarity of the electromagnets 5 can then be reversed and they will push away from the permanent magnet 20 assisting the ventricle in filling. This electromagnetic pumping system is novel in the way that multiple free-standing magnetic components generate magnetic fields that interact with one another to create mechanical force on diaphragms that can be used to assist both artificial and nature hearts. An electromagnetic pumping system has never been used to assist a heart through the linear interaction of magnetic field through the heart ventricle.

The use of wireless charging will allow for the devices to be charged from and external source. This source may be the battery belt 113 or some other power source. One alternative power source may be a bed charging system which will pull power from a conventional wall outlet and use a larger version of the wireless charging transmitter 112 to create a charging field around the whole bed. This will allow the patient to sleep without the need for any wires connected to them.

What we claim is:

1. A control system comprising:
   at least one permanent magnet configured to attach to a median septum of a heart;
   at leas one electromagnet configured to implant on a wall of the heart to assist the heart to at least one of contract and expand;
   an electromagnetic driver configured to control the at least one electromagnet; and
   a processor configured to control the electromagnetic driver based on input input received from an electrocardiogram electrode and input from at least one of a blood oxygen sensor, an accelerometer, a blood pressure sensor, an altimeter sensor, and a body temperature sensor.

2. The control system of claim 1, wherein the control system further includes a memory with instructions for controlling at least one electromagnet in accordance with at least one of heart rate, blood oxygen level, and blood pressure and historical data.

3. The control system of claim 2, further comprising:
   a receiver to allow for remote monitoring.

4. The control system of claim 3, further comprising:
   a battery configured to power the processor and the at least one electromagnet.

5. A heart assist device comprising:
   the control system of claim 1; and
   a power system, wherein the power system includes an induction receiver coil configured to charge a battery.

6. The heart assist device of claim 5, wherein the power system and the control system are connected and the power system provides electrical energy to the control system.

7. The heart assist system of claim 6, further comprising:
   at least one lead connected to of the at least one electromagnet; and
   the electrocardiogram electrode.

8. The heart assist system of claim 7, further comprising:
   at least one sensor configured to sense at least one of blood pressure and blood oxygen level and the control system is configured to control the heart at least partly based on the blood pressure and blood oxygen level.

9. A method of controlling a heart, comprising:
   monitoring a condition of the heart using at least one of an optic/sonic sensor, a strain gauge, and an electrocardiogram electrode;
   sending a signal indicative of a condition of the heart to the control system of claim 1, the processor configured to compare the condition to a preset value and control the electromagnetic driver based on the condition; and
   using the electromagnetic driver to energize the at least one electromagnet.

10. The method of claim 9, wherein the at least one electromagnet includes a first plurality of electromagnets arranged on an outside of a first ventricle wall and the processor controls the plurality of electromagnets to cause the first ventricle to contract and expand in a rhythmic manner.

11. The method of claim 10, wherein the at least one electromagnet includes a second plurality of magnets on an outside of a second ventricle wall and the processor controls the second plurality of electromagnets to cause the second ventricle to contract and expand in a rhythmic manner.

12. The method of claim 11, wherein the at least one electromagnet includes an electromagnet on an outside wall of a first atrium and another electromagnet on an outside wall of a second atrium.

13. The method of claim 12, wherein the electromagnetic driver simultaneously controls the first plurality of electromagnets, the second plurality of electromagnets, the electromagnet on the outside wall of the first atrium and the electromagnet on the outside wall of the second atrium in a manner that allows the heart to beat in a normal manner.

* * * * *

UNITED STATES PATENT AND TRADEMARK OFFICE
CERTIFICATE OF CORRECTION

PATENT NO.         : 10,918,772 B1
APPLICATION NO.    : 16/139811
DATED              : February 16, 2021
INVENTOR(S)        : Dillion Gene Hurd Page 1 of 1

It is certified that error appears in the above-identified patent and that said Letters Patent is hereby corrected as shown below:

In the Claims

Column 11, Lines 25-38, should read:
1. A control system comprising: at least one permanent magnet configured to attach to a median septum of a heart; at least one electromagnet configured to implant on a wall of the heart to assist the heart to at least one of contract and expand; an electromagnetic driver configured to control the at least one electromagnet; and a processor configured to control the electromagnetic driver based on input received from an electrocardiogram electrode and input from at least one of a blood oxygen sensor, an accelerometer, a blood pressure sensor, an altimeter sensor, and a body temperature sensor.

Signed and Sealed this
Twentieth Day of April, 2021

Drew Hirshfeld
*Performing the Functions and Duties of the*
*Under Secretary of Commerce for Intellectual Property and*
*Director of the United States Patent and Trademark Office*